(12) United States Patent
Chiba et al.

(10) Patent No.: US 10,279,100 B2
(45) Date of Patent: May 7, 2019

(54) INDWELLING NEEDLE FOR EXTRACORPOREAL CIRCULATION

(71) Applicant: NIKKISO CO., LTD., Tokyo (JP)

(72) Inventors: Toshiaki Chiba, Tokyo (JP); Masato Fujiwara, Higashimurayama (JP); Satoru Horioka, Higashimurayama (JP)

(73) Assignee: NIKKISO CO., LTD., Tokyo (JP)

( * ) Notice: Subject to any disclaimer, the term of this patent is extended or adjusted under 35 U.S.C. 154(b) by 476 days.

(21) Appl. No.: 14/431,023

(22) PCT Filed: Sep. 30, 2013

(86) PCT No.: PCT/JP2013/076524
§ 371 (c)(1),
(2) Date: Mar. 25, 2015

(87) PCT Pub. No.: WO2014/051138
PCT Pub. Date: Apr. 3, 2014

(65) Prior Publication Data
US 2015/0246172 A1 Sep. 3, 2015

(30) Foreign Application Priority Data
Sep. 28, 2012 (JP) .................................. 2012-216266

(51) Int. Cl.
*A61M 1/30* (2006.01)
*A61M 1/36* (2006.01)
A61M 25/06 (2006.01)

(52) U.S. Cl.
CPC ............ *A61M 1/3659* (2014.02); *A61M 1/30* (2013.01); *A61M 25/0643* (2013.01)

(58) Field of Classification Search
CPC .... A61M 1/3659; A61M 1/3661; A61M 1/30; A61M 1/14; A61M 25/0643;
(Continued)

(56) References Cited

U.S. PATENT DOCUMENTS 4,180,068 A * 12/1979 Jacobsen ............... A61B 17/34
604/164.01
4,202,332 A 5/1980 Tersteegen et al.
(Continued)

FOREIGN PATENT DOCUMENTS

GB 2032778 A * 5/1980 .......... A61M 5/1582
JP S53-093686 A 8/1978
(Continued)

OTHER PUBLICATIONS

Jan. 14, 2014 International Search Report issued in International Application No. PCT/JP2013/076524.

*Primary Examiner* — Kevin C Sirmons
*Assistant Examiner* — Leah J Swanson
(74) *Attorney, Agent, or Firm* — Oliff PLC (57) ABSTRACT

A seal member and outer cylinder needle (OCN) tip part for blocking, in a fluid-tight state, both external peripheral space (EPS) end parts formed between the external-peripheral-surface of an inner needle (IN) and internal peripheral surface of an OCN, for slidably holding the IN in close contact; an opening part formed on the OCN external-peripheral-surface and for intravascular communication with the EPS; an OCN connection part for communicating between the EPS and blood circuit end; an IN connection part for communicating between the IN internal space and other blood circuit end. The movable IN positioned between the projecting position where the tip part protrudes from the OCN tip and the housed position housing the tip inside the OCN. The IN punctures the blood vessel interior while holding the projecting position, and moved to the housed position after puncture allowing blood to extracorporeally circulate via the OCN and IN connection part.

11 Claims, 4 Drawing Sheets

(58) Field of Classification Search
CPC .............. A61M 25/0606; A61M 29/00; A61M 2025/0175; A61M 1/3621; A61M 1/3653; A61M 25/0026; A61M 25/0071
USPC ..................................................... 604/164.01
See application file for complete search history.

(56) References Cited

U.S. PATENT DOCUMENTS

| | | | |
|---|---|---|---|
| 4,217,895 A | 8/1980 | Sagae et al. | |
| 4,299,217 A | 11/1981 | Sagae et al. | |
| 4,493,696 A | 1/1985 | Uldall | |
| 5,531,701 A * | 7/1996 | Luther | A61M 25/0069 604/165.04 |
| 5,893,844 A | 4/1999 | Misawa | |
| 6,547,762 B1 * | 4/2003 | Botich | A61M 25/0631 604/110 |
| 2003/0153873 A1 * | 8/2003 | Luther | A61M 25/0606 604/158 |
| 2004/0097819 A1 * | 5/2004 | Duarte | A61B 5/0422 600/509 |
| 2009/0105651 A1 * | 4/2009 | Wada | A61M 5/158 604/164.01 |
| 2009/0163942 A1 * | 6/2009 | Cuevas | A61M 16/0472 606/167 |

FOREIGN PATENT DOCUMENTS

| | | |
|---|---|---|
| JP | S54-295 U | 1/1979 |
| JP | S56-100066 A | 8/1981 |
| JP | S56-0139762 A | 10/1981 |
| JP | S64-043938 A | 3/1989 |
| JP | H01-212567 A | 8/1989 |
| JP | H04-026110 A | 6/1992 |
| JP | 3073713 B2 | 8/2000 |
| WO | 2006/022025 A1 | 3/2006 |

* cited by examiner

INDWELLING NEEDLE FOR EXTRACORPOREAL CIRCULATION

TECHNICAL FIELD

The present invention relates to an indwelling needle for extracorporeal circulation for use by being punctured into and dwelling in a blood vessel of a patient when conducting extracorporeal circulation of blood.

BACKGROUND ART

In blood extracorporeal circulation (for example, blood extracorporeal circulation for blood purification treatment such as dialysis or the like), conventionally, an indwelling needle is punctured into to indwell in a blood vessel of a patient, and a blood circuit is connected to the indwelling needle. In general, one indwelling needle indwells in each of an artery and a vein, and these indwelling needles are connected to the respective ends of a blood circuit (see Patent Document 1, for example).

However, it is painful for a patient to have two indwelling needles dwelling in his/her blood vessel throughout the entire period of blood extracorporeal circulation. In addition, when two indwelling needles are used, there is a problem that, should a needle for receiving blood (on the vein side) be removed, a large amount of blood will be poured to the outside. In view of the above, in order to avoid use of two indwelling needles, there has been known a single indwelling needle having a structure in which a unit for connection to a blood circuit is branched into two so that one branched connection portion is connected to an inlet end of the blood circuit and the other to a discharge end of the blood circuit (for example, see Patent Document 2).

However, an indwelling needle having a connection portion simply branched into two requires provision of an inlet pump for introducing blood from the indwelling needle and a discharge pump for discharging blood to the indwelling needle. This results in a complicated structure of a, blood circuit. Moreover, as it is necessary to alternately conduct blood introducing operation and blood discharging operation, poor efficiency in blood extracorporeal circulation results. In order to address the above-described inconvenience, it is preferable to form an indwelling needle having a double lumen structure to ensure separate introducing and discharging passages (see Patent Document 3, for example).

CITATION LIST

Patent Literature

Patent Document 1: JP 3073713 B
Patent Document 2: JP H4-26110 U
Patent Document 3: WO 2006/022025 A

SUMMARY OF INVENTION

Technical Problem

However, an indwelling needle in a simple double lumen structure has a problem that the tip end portion thereof is inevitably finished thick, which increases pain for a patient punctured by the needle. Moreover, as the inner needle is removed while the needle is dwelling in a blood vessel, it is possible that the tip end of the removed inner needle erroneously pricks a person involved in operation (that is, a nurse or a patient on home dialysis).

The present invention has been conceived in view of the above, and aims to achieve a double lumen structure without an excessively thick tip end portion of a needle to thereby provide an indwelling needle for extracorporeal circulation capable of reducing inconvenience due to severe pain caused when puncturing a needle into a blood vessel, and free from a possibility that the tip end portion of the inner needle removed erroneously pricks a person involved in operation.

Solution to Problem

The present invention has been conceived in order to achieve the above-described object, and according to claim 1, there is provided an indwelling needle for extracorporeal circulation having a double tube structure including an outer needle made of a tube member having an opening formed on a tip end thereof, and an inner needle made of a tube member having a puncture portion formed on a tip end thereof and inserted in the outer needle, including: a holding member for closing, in a liquid-tight state, respective ends of an outer circumferential space formed between an outer circumferential surface of the inner needle and an inner circumferential surface of the outer needle, and for closely holding the inner needle in a slidabale state; a hole formed on an outer circumferential surface of the outer needle on a tip end side thereof in a position further rearward than the holding member, for communicating between the interior of a blood vessel and the outer circumferential space when being punctured into the blood vessel; a first connection portion for communicating between the outer circumferential space and one end portion of a blood circuit; and a second connection portion for communicating between an inner space of the inner needle and another end portion of the blood circuit, wherein the inner needle is held by the holding member so as to move between a projecting position where an tip end portion thereof projects from a tip end of the outer needle and a housed position where the tip end portion thereof is housed in the outer needle, and the inner needle is punctured into the blood vessel while being held in the projecting position, and then moved to the housed position after being punctured so that blood extracorporeal circulation is able to be conducted via the first connection portion and the second connection portion.

According to claim 2, there is provided an indwelling needle for extracorporeal circulation according to claim 1, wherein the holding member positioned on a tip end side of the outer needle may be a tip end portion of the outer needle attached to a tip end portion of a longitudinal tube-like outer needle main body.

According to claim 3, there is provided an indwelling needle for extracorporeal circulation according to claim 1, wherein the holding member positioned on a tip end side of the outer needle may be a tip end portion of the outer needle that is formed by thinning a tip end portion of a longitudinal tube-like outer needle main body so as to have a reduced diameter.

According to claim 4, there is provided an indwelling needle for extracorporeal circulation according to claim 1, wherein the hole may be an inlet through which to introduce blood from the blood vessel, and a tip end opening of the inner space of the inner needle may be a return opening through which to return into the blood vessel blood having circulated in the blood circuit.

According to claim 5, there is provided an indwelling needle for extracorporeal circulation according to claim 1, wherein the first connection portion may have a movement guide portion for guiding the second connection portion along a movement direction of the inner needle.

According to claim 6, there is provided an indwelling needle for extracorporeal circulation according to claim 1, wherein the second connection portion may have an inner needle movement operation unit projecting toward the outside of the second connection portion.

According to claim 7, there is provided an indwelling needle for extracorporeal circulation according to claim 1, wherein one of the first connection portion and the second connection portion may have an engaged member, and the other has an engagement portion with which the engaged member is able to be engaged, and the engagement portion may include a projecting engagement portion with which the engaged member in the projecting position may be engaged and a housed engagement portion with which the engaged member in the housed position is engaged.

According to claim 8, there is provided an indwelling needle for extracorporeal circulation according to claim 7, further including an engaged guide portion provided between the projecting engagement portion and the housed engagement portion, for guiding the engaged member along a movement direction of the inner needle.

According to claim 9, there is provided an indwelling needle for extracorporeal circulation according to claim 1, further including an urging member provided between the first connection portion and the second connection portion, for urging the inner needle in a direction from the projecting position to the housed position, and when engagement between the engaged member and the projecting engagement portion is released, the second connection portion may be urged by an urging force of the urging member whereby the inner needle moves from the projecting position to the housed position.

According to claim 10, there is provided an indwelling needle for extracorporeal circulation according to claim 1, wherein the outer diameter of the inner needle may be set smaller than an inner diameter of a longitudinal tube-like outer needle main body so that the outer circumferential space is formed to be cylindrical between the outer circumferential surface of the inner needle and an inner circumferential surface of the outer needle main body.

Advantageous Effect of Invention

According to the present invention, advantageous effects described below are obtained.

According to the invention defined in claim 1, the inner needle punctured in the blood vessel can be utilized as a part of a blood circulation passage, rather than being pulled out. This can eliminate the need for preparing a member only for puncture into a blood vessel separately from a member constituting a blood circulation passage. This makes it possible to achieve an indwelling needle for extracorporeal circulation having a double lumen structure without an excessively thick tip end portion, which can reduce inconvenience with severe pain caused during puncture into a blood vessel. Further, as it is unnecessary to pull out the inner needle from the outer needle, there is no possibility that the puncture unit of the inner needle erroneously pricks a person involved in operation (a person preparing for blood extracorporeal circulation). Still further, as the inner needle is moved to the housed position, it is possible to prevent the puncture unit of the inner needle from being exposed in a blood vessel. This can avoid inconvenience that the puncture unit of the inner needle unintentionally damages a blood vessel while the indwelling needle for extracorporeal circulation is dwelling in the blood vessel.

According to the invention defined in claim 2, as the holding member positioned on the tip end side of the outer needle is a tip end portion of the outer needle attached to the tip end portion of a longitudinal tube-like outer needle main body, it is easier to manufacture the tip end portion of the outer needle, using a harder material than that used for the outer needle main body. This makes it easier to implement an outer needle that can facilitate puncture.

According to the invention defined in claim 3, as the holding member positioned on the tip end side of the outer needle is a tip end portion of the outer needle that is made by thinning the tip end portion of a longitudinal tube-like outer needle main body so as to have a reduced diameter, it is unnecessary to form the tip end portion of the outer needle separately from the outer needle main body. This can reduce manufacturing cost.

According to the invention defined in claim 4, as the hole is an inlet through which to introduce blood from a blood vessel, and the tip end opening of the inner space of the inner needle is an outlet through which to return back to the blood vessel blood having circulated in the blood circuit, it is possible to avoid inconvenience that blood is poured from the hole even when the indwelling needle for extracorporeal circulation indwelling is unintentionally partially removed from the blood vessel and the hole is thereby exposed to the outside.

According to the invention defined in claim 5, as the first connection portion has a movement guide portion for guiding the second connection portion along the movement direction of the inner needle, it is possible to smoothly move the inner needle, and thus to promptly execute an indwelling preparation operation for an indwelling needle for extracorporeal circulation.

According to the invention defined in claim 6, as the second connection portion has an inner needle movement operation unit projecting outward of the second connection portion, it is possible to more readily move the inner needle.

According to the invention defined in claim 7, as one of the first connection portion and the second connection portion has an engaged member and the other has an engagement portion with which the engaged member can be engaged, and the engagement portion includes a projecting engagement portion with which the engaged member in the projecting position is engaged and a housed engagement portion with which the engaged member in the housed position is engaged, it is possible to achieve proper positioning of the inner needle in the projecting position and the housed position. Therefore, it is possible to promptly execute a movement operation for moving the inner needle; in particular, a movement operation for movement from the projecting position to the housed position after puncture into a blood vessel, and thus to efficiently execute an indwelling preparation operation for an indwelling needle for extracorporeal circulation. Further, it is possible to prevent unintentional displacement of the inner needle having been positioned. With the above, it is possible to avoid inconvenience that the tip end portion of the inner needle moves to be housed in the outer needle when puncturing an indwelling needle for extracorporeal circulation into a blood vessel or that the tip end portion of the inner needle projects from the outer needle while the outer needle is dwelling in a blood vessel.

According to the invention defined in claim 8, as an engaged guide portion for guiding an engaged member along the movement direction of the inner needle is provided between the projecting engagement portion and the housed engagement portion, it is possible to more readily move the inner needle.

According to the invention defined in claim 9, as there is provided an urging member between the first connection portion and the second connection portion, for urging the inner needle in a direction from the projecting position to the housed position, and when engagement between the engaged member and the projecting engagement portion is released, the second connection portion is urged by an urging force of the urging member whereby the inner needle is caused to move from the projecting position to the housed position, it is possible to conduct a movement operation for moving the inner needle to the housed position simply by releasing the engaged member from the projecting engagement portion. This makes it possible to promptly execute an indwelling preparation operation for an indwelling needle for extracorporeal circulation.

According to the invention defined in claim 10, as the outer diameter of the inner needle is set smaller than the inner diameter of a longitudinal tube-like outer needle main body so that the outer circumferential space is formed to be cylindrical between the outer circumferential surface of the inner needle and the inner circumferential surface of the outer needle main body, it is possible to form the outer circumferential space between the outer circumferential surface of the inner needle and the inner circumferential surface of the outer needle, by means of a simple structure. Further, it is possible to ensure a large cross section of the outer circumferential space, and to achieve a structure for facilitating blood circulation without backset.

DESCRIPTION OF EMBODIMENTS

Figure 1:
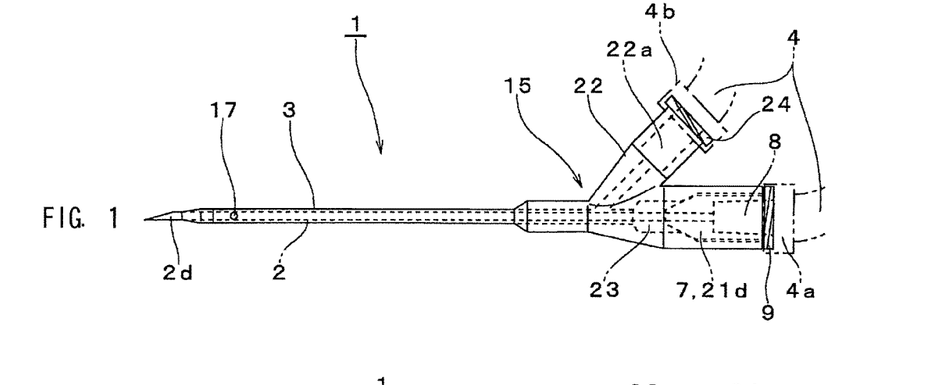
FIG. 1 shows the external appearance of an indwelling needle for extracorporeal circulation.
Figure 2A:
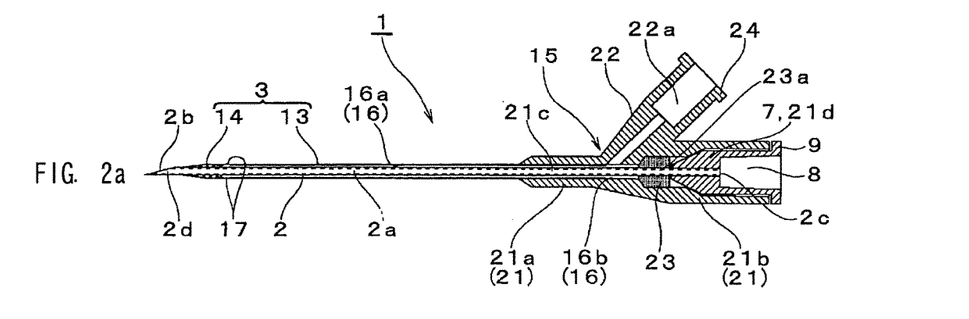
FIG. 2a is a cross sectional view of an inner needle of an indwelling needle for extracorporeal circulation having moved to a projecting position.
Figure 2B:
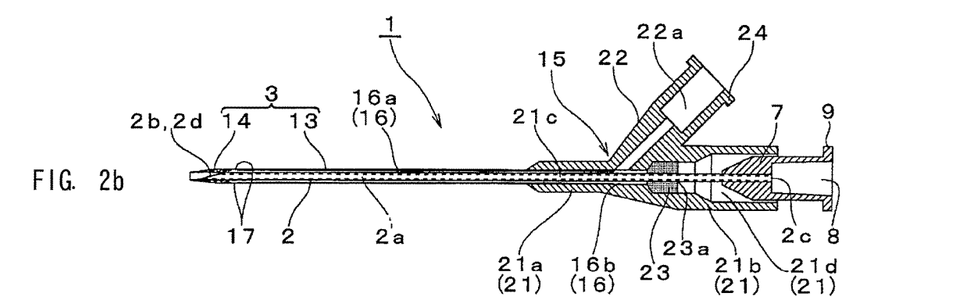
FIG. 2b is a cross sectional view of an inner needle of an indwelling needle for extracorporeal circulation having moved to a housed position.

In the following, embodiments of the present invention will be described by reference to the drawings. As shown in FIGS. 1 and 2, an indwelling needle for extracorporeal circulation 1 has an inner needle 2 and an outer needle 3, each made of a tube. The inner needle 2 is inserted in the outer needle 3, whereby a double-tube structure is formed. The tip end portion of the inner needle 2 and that of the outer needle 3 are sharpened so that these can be punctured into a blood vessel of a patient. A base end portion of the inner needle 2 and that of the outer needle 3 are connected to a blood circuit 4 for extracorporeal circulation of blood of a patient so that blood can circulate between a blood vessel and the blood circuit 4.

The inner needle 2 is made of a thin long metallic tube. An inner space 2a where blood can flow is formed inside the inner needle 2 so as to extend throughout the entire length of the inner needle 2. A tip end opening 2b and a base end opening 2c are defined on respective both ends of the inner space 2a so that the inner space 2a is exposed outward through the holes 2b, 2c. The tip end portion of the inner needle 2 with the tip end opening 2b defined therein (the left end portion in FIG. 2a) has a puncture unit 2d.

Meanwhile, the base end portion of the inner needle 2 with the base end opening 2c defined therein (the right end portion in FIG. 2a) has an inner needle connection portion 7 (corresponding to the second connection portion according to the present invention). The inner needle connection portion 7 is a plastic cylindrical member positioned coaxial to the inner needle 2, and an inner needle communicating space 8 is formed inside the inner needle connection portion 7. The end of the inner needle communicating space 8 on the inner needle 2 side (the left side in FIG. 2a) communicates with the base end opening 2c of the inner needle 2, while the other end on the opposite side from the inner needle 2 with the middle portion of the inner needle communicating space 8 in-between (the right side in FIG. 2a) is exposed outward. An inner needle side male screw 9 is formed on the outer circumference of the inner needle connection portion 7 in a position on the released end side of the inner needle communicating space 8, so that a lock ring 4a (see FIG. 1) mounted on an end portion of the blood circuit 4 can be threaded into the inner needle side male thread 9. When the end portion of the blood circuit 4 is set abutting on the released opening and the lock ring 4a is then screwed onto the inner needle side male thread 9, the blood circuit 4 and the inner needle connection portion 7 are closely adhered to each other in a liquid-tight state, as a result of which the blood circuit 4 communicates with the inner space 2a through the inner needle communicating space 8 inside the inner needle connection portion 7.

The outer needle 3 can indwell in a blood vessel. The outer needle 3 includes an outer needle main body 13 and an outer needle tip end portion 14. The inner needle 2 is inserted in the outer needle main body 13 so that the puncture portion 2d can project from the tip end of the outer needle main body 13. The outer needle tip end portion 14 is attached to the tip end portion of the outer needle main body 13 as a tip end portion of the outer needle 3. An outer needle connection portion 15 (corresponding to the first connection portion according to the present invention) is connected to the base end portion (the right end in FIG. 2a) of the outer needle 3.

Figure 3A:
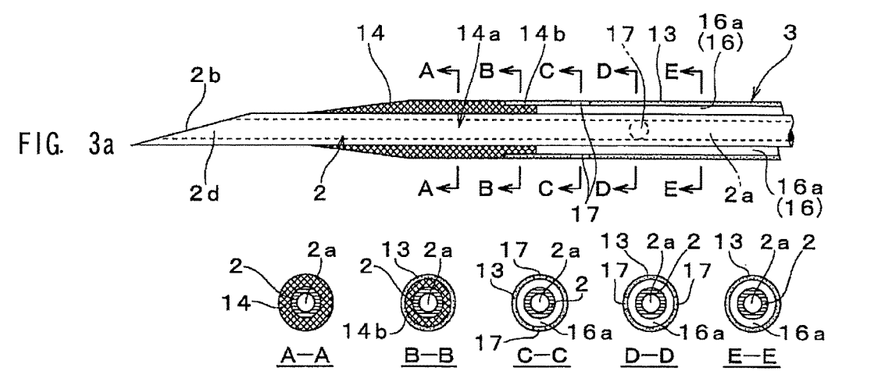
FIG. 3a is a diagram explaining an inner needle of an indwelling needle for extracorporeal circulation having moved to a projecting position, and showing cross sections at respective positions.
Figure 3B:
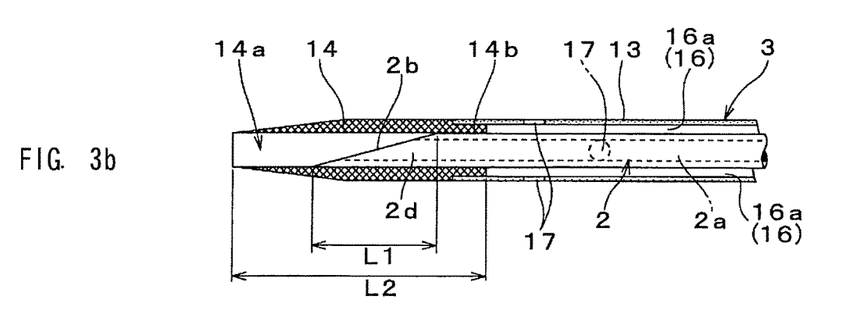
FIG. 3b is a diagram explaining an inner needle of an indwelling needle for extracorporeal circulation having moved to a housed position.

As shown in FIGS. 2 and 3, the outer needle main body 13 is a longitudinal cylindrical member made of flexible plastic (for example, polypropylene or polyethylene), whose outer diameter is set equal to that of the outer needle tip end portion 14 so as to avoid formation of a step between the outer needle main body 13 and the outer needle tip end portion 14. Further, as shown in FIG. 3a, the inner diameter of the outer needle main body 13 is set larger than the outer diameter of the inner needle 2 (in other words, the outer diameter of the inner needle 2 is set smaller than the inner diameter of the outer needle main body 13), so that a part (a tip end side part) 16a of an outer circumferential space 16 where blood can flow is formed to be cylindrical between the outer circumferential surface of the inner needle 2 and the inner circumferential surface of the outer needle main body 13. Further, two or more (four in this embodiment) holes 17 are formed on the outer circumferential surface of the outer needle main body 13 at positions closer to the outer needle tip end portion 14 so that the outer circumferential space 16 is exposed through these holes 17. Specifically, the holes 17 are formed on the outer needle 3 on the tip end side thereof at positions further rearward than the outer needle tip end portion 14 (in other words, a position displaced toward the base end portion of the outer needle 3 in relation to the outer needle tip end portion 14). In this embodiment, two holes 17 are formed at positions closer to the outer needle tip end portion 14, and another two holes 17 are formed at positions displaced toward the outer needle connection portion 15 side by a few mm from the former holes 17. The two holes 17 closer to the outer needle tip end portion 14 are positioned displaced in phase by 180 degrees as viewed in the circumferential direction of the outer needle 3, and the other two holes 17 closer to the outer needle connection portion 15 are positioned displaced in phase by 90 degrees relative to the respective holes 17 closer to the outer needle tip end portion 14 as viewed in the circumferential direction of the outer needle 3.

The outer needle tip end portion 14 attached to the tip end portion of the outer needle main body 13 is a short cylindrical component made of plastic harder than the outer needle main body 13, and has a thinner tip end portion. The entire length of the outer needle tip end portion 14 is set to a length L2 sufficiently longer than the length L1 of the puncture portion 2d (see FIG. 3b). That is, the outer needle 3 has a tapered thin tip end portion. A penetrating space 14a is formed inside the outer needle tip end portion 14, and the puncture portion 2d of the inner needle 2 inserted in the outer needle 3 can be housed in the penetrating space 14a. The inner diameter of the outer needle tip end portion 14 is set equal to or slightly smaller than the outer diameter of the inner needle 2, so that the inner circumferential surface of the outer needle tip end portion 14 maintains close contact with the outer circumferential surface of the inner needle 2 in a slidable and liquid-tight state. With the above, the outer needle tip end portion 14 closes the end of the outer circumferential space 16 in a liquid-tight state such that the tip end opening 2b of the inner needle 2 does not communicate with the outer circumferential space 16. Further, the outer needle tip end portion 14 functions as a part of a holding member in the present invention for closely holding the tip end portion of the inner needle 2 in a slidable state. Still further, in the base portion of the outer needle tip end portion 14 (an end portion positioned on the outer needle main body 13 side), a joint portion 14b having a reduced diameter is formed for insertion into the outer needle main body 13. The outer circumferential surface of the joint portion 14b is held in close contact with the inner circumferential surface of the outer needle main body 13 in a liquid-tight state.

The outer needle 3 including the outer needle tip end portion 14 and the outer needle main body 13 may be formed, for example, by means of insert molding by inserting the outer needle tip end portion 14 into an end portion of the outer needle main body 13 prepared in advance. Alternatively, the outer needle tip end portion 14 and the outer needle main body 13 may be separately molded in advance, and the outer needle main body 13 and the joint portion 14b inserted in the outer needle main body 13 are then adhered or welded to each other.

The outer needle connection portion 15 connected to the base end portion (the right end portion in FIG. 2a) of the outer needle main body 13 is a substantially y-shaped plastic member that is formed by integrally molding a connection portion main body 21 and a branched portion 22, in which the connection portion main body 21 is positioned coaxially with the inner needle 2 and the outer needle 3, and the branched portion 22 is branched from the connection portion main body 21, as shown in FIGS. 1 and 2. The inner needle connection portion 7 can be housed in the connection portion main body 21, with the inner needle 2 inserted in the outer needle 3. One end portion of the blood circuit 4 can be connected to the branched portion 22. Specifically, the connection portion main body 21 has a cylindrical shape positioned coaxially with the inner needle 2 and the outer needle 3. The tip end portion 21a of the connection portion main body 21, to which the outer needle 3 is connected, is formed having a smaller diameter than that of the base end portion 21b where the inner needle connection portion 7 can be housed. An insertion space 21c for inserting the inner needle 2 into the outer needle 3 is formed to penetrate the tip end portion 21a of the connection portion main body 21 along the central axis of the connection portion main body 21. A part (a part within the base portion) of the outer circumferential space 16 is formed to be cylindrical between the inner circumferential surface of the insertion space 21c and the outer circumferential surface of the inner needle 2 so as to communicate with the tip end side portion 16a of the outer circumferential space 16 inside the outer needle 3. The housing space 21d larger than the inner needle connection portion 7 is formed in the base end portion 21b of the connection portion main body 21 so as to communicate with the insertion space 21c (see FIG. 2b). The end (the right side in FIG. 2a) of the housing space 21d on the opposite side from the tip end portion 21a of the connection portion main body 21 with the middle portion of the housing space 21d in-between is released so that the inner needle connection portion 7 can be inserted into the housing space 21d with the inner needle side male thread 9 exposed outward from the released opening.

At a position where the housing space 21d communicates with the insertion space 21c; in other words, in an insertion opening of the insertion space 21c through which the inner needle 2 is to be inserted, a seal member 23, made of silicon rubber or the like, is attached to close the insertion opening of the insertion space 21c. A seal-penetrating hole 23a having a smaller diameter than that of the inner needle 2 is formed to penetrate the seal member 23 along the extension line of the insertion space 21c. The seal member 23 (in detail, the inner circumferential surface of the seal penetrating hole 23a) is kept in close contact with the outer circumferential surface of the inner needle 2 in a slidable and liquid-light state. With the above, the seal member 23 closes the base end of the outer circumferential space 16 in a liquid-tight state so that the housing space 21d does not communicate with the outer circumferential space 16. The seal member 23 functions also as a part of the holding member in the present invention for closely holding the base end portion of the inner needle 2 in a slidabale state.

The branched portion 22 has a cylindrical shape branched from the lateral surface of the tip end portion 21a of the connection portion main body 21 and projecting toward the lateral side of the base end portion 21b of the connection portion main body 21. Inside the branched portion 22, a branched communicating space 22a is formed branched from the insertion space 21c and extending along the axial direction of the branched portion 22. A part of the branched communicating space 22a positioned on the projecting end portion side of the branched portion 22 is formed having a larger diameter than that of a part of the same positioned on the insertion space 21c side, and exposed outward from the projecting end portion. A branch side male thread 24 is formed on the external circumference of the branched portion 22 in a position on the exposed opening side of the branched communicating space 22a so that a lock ring 4b mounted on an end portion of the blood circuit 4 can be screwed onto the branch side male thread 24 (see FIG. 1). When an end portion of the blood circuit 4 is held abutting on the released opening and the lock ring 4b is then screwed onto the branch side male thread 24, the blood circuit 4 and the branched portion 22 are kept in close contact with each other in a liquid-tight state, as a result of which the blood circuit 4 communicates with the outer circumferential space 16 via the insertion space 21c and the branched communicating space 22a inside the outer needle connection portion 15.

In the indwelling needle for extracorporeal circulation 1 having the above-described structure, when the inner needle connection portion 7 is sufficiently advanced toward the outer needle 3 side with the inner needle 2 inserted in the outer needle 3, the inner needle 2 will move to the projecting position while being held on the respective ends thereof by the seal member 23 and the outer needle tip end portion 14, as shown in FIGS. 2a and 3a. As a result, the inner needle connection portion 7 abuts on the inner walls of the seal member 23 and the housing space 21d, and the puncture portion 2d projects from the outer needle 3. With the above, the tip end portion of the indwelling needle for extracorporeal circulation 1 is ready to be punctured into a blood vessel. When the needle connection portion 7 is pulled out with the inner needle 2 held in the projecting position, the inner needle 2 will move to a housed position while being held on the respective ends thereof by the seal member 23 and the outer needle tip end portion 14, as shown in FIGS. 2b and 3b, and the puncture portion 2d is housed in the outer needle 3.

To conduct extracorporeal circulation of blood of a patient, using the indwelling needle for extracorporeal circulation 1, initially, one end portion of the blood circuit 4 is set connected to the outer needle connection portion 15, and the other end portion to the inner needle connection portion 7. With the above, the one end portion of the blood circuit 4 communicates with the branched communicating space 22a, the outer circumferential space 16, and the hole 17, while the other end portion of the blood circuit 4 communicates with the inner needle communicating space 8 and the inner space 2a. After the blood circuit 4 is connected to the indwelling needle for extracorporeal circulation 1, the tip end portion (specifically, the puncture portion 2d projecting from the outer needle tip end portion 14) of the indwelling needle for extracorporeal circulation 1 is punctured into a blood vessel of a patient, with the inner needle 2 held in the projecting position by the seal member 23 and the outer needle tip end portion 14. Then, the indwelling needle 1 is inserted until the hole 17 formed on the lateral side of the outer needle main body 13 sufficiently enters the blood vessel, as a result of which the inside of the blood vessel communicates with the outer circumferential space 16 through the hole 17.

After the indwelling needle for extracorporeal circulation 1 is punctured into the blood vessel, the inner needle connection portion 7 is retreated (pulled out) to move the inner needle 2 from the projecting position to the housed position. As a result, the puncture portion 2d is housed in the outer needle tip end portion 14. With the above, the blood vessel communicates with one end portion of the blood circuit 4 through the hole 17, the outer circumferential space 16, and the branched communicating space 22a, and also with the other end portion of the blood circuit 4 via the outer needle tip end portion 14, the puncture portion 2d housed in the outer needle tip end portion 14, the inner space 2a, and the inner needle communicating space 8. That is, it is possible to utilize the inner needle 2 punctured into the blood vessel as a part of a blood circulation passage, rather than being pulled out. This can eliminate the need for preparing a member only for puncture into a blood vessel separately from a member constituting a blood circulation passage. This makes it possible to achieve an indwelling needle for extracorporeal circulation 1 having a double lumen structure without an excessively thick tip end portion, which in turn can reduce inconvenience with severe pain caused in puncture into a blood vessel. Further, as it is unnecessary to pull out the inner needle 2 from the outer needle 3, there is no possibility that the puncture portion 2d erroneously pricks a person involved in operation (a person preparing for blood extracorporeal circulation). Still further, as the inner needle 2 is moved to the housed position, it is possible to prevent the puncture portion 2d from being exposed in a blood vessel. This can avoid inconvenience that the puncture portion 2d of the indwelling needle for extracorporeal circulation 1 unintentionally damages a blood vessel while the indwelling needle for extracorporeal circulation 1 is dwelling in the blood vessel. Yet further, as puncture of the indwelling needle for extracorporeal circulation 1 into a blood vessel is completed with only one puncture operation, it is preferable, as the number of occasions when a patient feels pain is fewer than that in a case where two indwelling needles are punctured into a blood vessel (specifically, a case where an indwelling needle for introducing blood into the blood circuit 4 and an indwelling needle for returning blood from the blood circuit 4 are separately punctured).

The outer needle 3 is made by attaching the outer needle tip end portion 14 to the tip end portion of the longitudinal tube-like outer needle main body 13. This makes it easier to manufacture the outer needle tip end portion 14, using a harder material than the outer needle main body 13, which makes it easier to manufacture an outer needle 3 that can facilitate puncture. Moreover, when the outer needle tip end portion 14 is made of plastic, inconvenience that the inner wall of a blood vessel is damaged is unlikely to be caused even when a patient moves his/her body while the indwelling needle for extracorporeal circulation 1 is indwelling and the outer needle tip end portion 14 resultantly abuts on the inner wall of the blood vessel.

When the indwelling needle for extracorporeal circulation 1 is punctured into a blood vessel, the blood vessel communicates with one end portion of the blood circuit 4 via the outer needle 3 and the outer needle connection portion 15, and also with the other end portion of the blood circuit 4 via the inner needle 2 and the inner needle connection portion 7. Thereafter, a blood pump (not shown) connected midway in the blood circuit 4 is driven to cause the blood to circulate between the blood vessel and the blood circuit 4 via the indwelling needle for extracorporeal circulation 1. Specifically, blood in the blood vessel is introduced through the tip end opening 2b of the inner needle 2 to flow through the inner space 2a, the base end opening 2c, and the inner needle communicating space 8 into the other end portion of the blood circuit 4. Then, blood having flowed through the blood circuit 4 and discharged from one end portion of the blood circuit 4 now flows through the branched communicating space 22a and the outer circumferential space 16 to be discharged through the hole 17 of the outer needle 3 to be returned into the blood vessel.

Alternatively, blood in a blood vessel is introduced through the hole 17 of the outer needle 3 to flow through the outer circumferential space 16 and the branched communicating space 22a into one end portion of the blood circuit 4. Then, blood having flowed through the blood circuit 4 and discharged from the other end portion of the blood circuit 4 now flows through the inner needle communicating space 8, the base end opening 2c, and the inner space 2a to be discharged through the tip end opening 2b of the inner needle 2 to be returned back into the blood vessel. When the blood flows as described above; that is, when the hole 17 is an inlet through which to introduce blood from the blood vessel, and the outer needle tip end portion 14 and the puncture portion 2d are outlets through which to return the blood having circulated in the blood circuit 4 to the blood vessel, it is possible to avoid inconvenience that blood is poured from the hole 17 even when the indwelling needle for extracorporeal circulation 1 indwelling in a blood vessel is erroneously removed partially from the blood vessel and the holes 17 are thereby exposed to the outside. Also, it is possible to keep returning the blood from the blood circuit 4 to the blood vessel so long as the indwelling needle for extracorporeal circulation 1 remains punctured in the blood vessel.

Further, as a blood vessel communicates with the blood circuit 4 via the indwelling needle for extracorporeal circulation 1, it is possible to maintain continuous blood circulation irrespective of the direction of a blood flow. Therefore, it is possible to achieve superior efficiency in extracorporeal circulation, compared to an intermittent operation in which blood is alternately introduced and returned, using an indwelling needle having branched channels connected to a single needle. With the above, it is possible to avoid prolonging of a blood extracorporeal circulation period (for example, a dialysis time), and thus to lessen excessive burden imposed on a patient subjected to blood extracorporeal circulation.

Further, as the outer diameter of the inner needle 2 is set smaller than the inner diameter of the outer needle 3 to define a cylindrical outer circumferential space 16 between the outer circumferential surface of the inner needle 2 and the inner circumferential surface of the outer needle 3, it is possible to form the outer circumferential space 16 by means of a simple structure. Further, it is possible to ensure a large cross section of the outer circumferential space 16, and to achieve a structure for facilitating blood circulation without backset.

Note that although a structure for facilitating an operation for moving the inner needle 2 is not provided in the above-described first embodiment, the present invention is not limited to the above description. For example, a second embodiment shown in FIG. 4 is basically similar to the first embodiment, but different in that a slide mechanism for guiding the inner needle connection portion 7 in movement is provided.

Figure 4A:
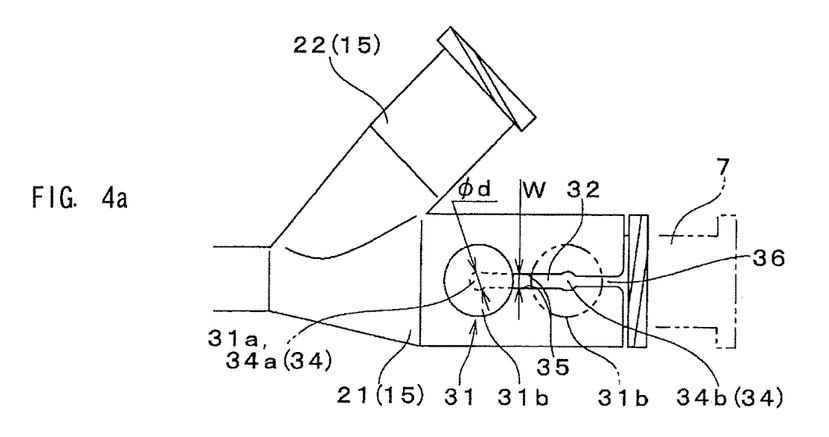
FIG. 4a shows external appearance of major members of an indwelling needle for extracorporeal circulation having a movement guide portion.
Figure 4B:
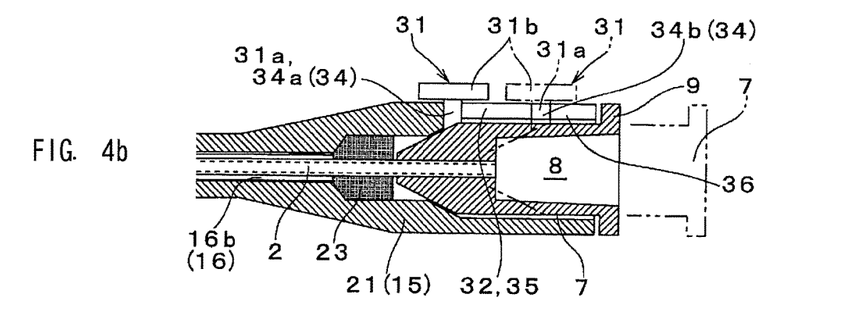
FIG. 4b shows external appearance of major members of an indwelling needle for extracorporeal circulation having a movement guide portion.

Specifically, as shown in FIG. 4, the inner needle connection portion 7 in the second embodiment has an inner needle movement operation unit 31 projecting outward from the outer circumferential portion of the inner needle connection portion 7. The inner needle movement operation unit 31 includes a cylindrical engaged member 31a projecting from the outer circumferential surface of the inner needle connection portion 7, and a disk-like movement operation piece 31b attached to the projecting end portion of the engaged member 31a and positioned outside the connection portion main body 21 of the outer needle connection portion 15. Further, a slit of a movement guide portion 32 is formed in the connection portion main body 21 of the outer needle connection portion 15 so as to extend along the movement direction of the inner needle 2 for engagement with the inner needle connection portion 7 via the engaged member 31a. The width size (the width size along the circumferential direction of the connection portion main body 21) W of the movement guide portion 32 is set slightly smaller than the diameter φd of the engaged member 31a (see FIG. 4a).

An engagement portion with which the engaged member 31a can be engaged is formed at each end of the movement guide portion 32. In detail, at the end of the movement guide portion 32 on the outer needle 3 side (the left side in FIG. 4a), a projecting engagement portion 34a is formed with which the engaged member 31a is engaged with the inner needle 2 having moved to the projecting position. Meanwhile, at the end of the movement guide portion 32 on the released end side (the right side in FIG. 4a) of the connection portion main body 21, a housing engagement portion 34a is formed with which the engaged member 31a is engaged with the inner needle 2 having moved to the housed position. Each of the projecting engagement portion 34a and the housing engagement portion 34b is defined by a hole having a diameter that is wider than the width size W of the movement guide portion 32 and allows stable holding of the engaged member 31a when engaged. Further, the slit edge of the movement guide portion 32 positioned between the projecting engagement portion 34a and the housing engagement portion 34b (a slit edge extending along the movement direction of the inner needle 2) is defined as an engagement guide portion 35 where the engaged member 31a can slide so that the engaged member 31a can be guided in the movement direction of the inner needle 2 along the engagement guide portion 35.

On the connection portion main body 21 of the outer needle connection portion 15, an entry notch slit 36 is formed on an extension line of the movement guide portion 32 on the housing engagement portion 34b side (the right side in FIG. 4a). The entry notch slit 36 has a width smaller than the width size W of the movement guide portion 32 and the diameter φd of the engaged member 31a, and is released at the end of the connection portion main body 21 so that the engaged member 31a passes along the entry notch slit 36 to reach the movement guide portion 32 when the inner needle 2 is assembled into the outer needle 3.

According to the indwelling needle for extracorporeal circulation 1 having the movement guide portion 32 and the inner needle movement operation unit 31 having the above-described structure, the engaged member 31a is kept engaged with the housing engagement portion 34b, as indicated by the long dashed double-short dashed line in FIG. 4, so that the inner needle 2 is held so as not to be displaced from the housed position until immediately before puncture into a blood vessel. With the above, it is possible to achieve proper positioning of the inner needle 2 in the housed position, and thus to avoid inconvenience that the inner needle 2 unintentionally moves to the projecting position and the puncture portion 2d accordingly projects from the outer needle 3, and resultantly, that the puncture portion 2d of the inner needle 2 having moved to the projecting position pricks and injures a person involved in operation. In puncturing into a blood vessel, the movement operation piece 31b of the inner needle movement operation unit 31 is pressed by a finger or the like to be slid from the housing engagement portion 34b side to the projecting engagement portion 34a side. With the above, the engaged member 31a is released from the housing engagement portion 34b, and the movement guide portion 32 (specifically, the engagement guide portion 35) guides the engaged member 31a and the inner needle connection portion 7 along the movement direction of the inner needle 2. Therefore, it is possible to smoothly move the inner needle 2, and thus to promptly execute an indwelling preparation operation for the indwelling needle for extracorporeal circulation 1. Further, as it is possible to move the inner needle 2 by operating the inner needle movement operation unit 31, it is possible to more readily move the inner needle 2.

When the inner needle movement operation unit 31 is sufficiently slid, the engaged member 31a is engaged with the projecting engagement portion 34a, as indicated by the solid line in FIG. 4, whereby the inner needle 2 is stably held so as not to be displaced from the projecting position. With the above, it is possible to achieve proper positioning of the inner needle 2 in the projecting position. After the inner needle 2 is positioned in the projecting position, the indwelling needle for extracorporeal circulation 1 is then punctured into a blood vessel. In the above, as the inner needle 2 is held at the projecting position by the engaged member 31a and the projecting engagement portion 34a, it is possible to avoid inconvenience that the inner needle 2 unintentionally moves from the projecting position to the housed position; in other words, inconvenience that the puncture portion 2d is pressed back into the outer needle 3 to disenable further puncture into a blood vessel even when the inner needle 2 is resisted by skin covering the blood vessel when puncturing.

When the indwelling needle for extracorporeal circulation 1 is punctured and inserted into a blood vessel until the hole 17 on the outer needle 3 enters the blood vessel, the movement operation piece 31b of the inner needle movement operation unit 31 is pressed by a finger or the like to be slid from the projecting engagement portion 34a side to the housing engagement portion 34b side. With the above, the engaged member 31a is released from the projecting engagement portion 34a, and the movement guide portion 32 (specifically, the engagement guide portion 35) guides the engaged member 31a and the inner needle connection portion 7 along the movement direction of the inner needle 2. Therefore, it is possible to smoothly move the inner needle 2 even after the indwelling needle for extracorporeal circulation 1 is punctured into a blood vessel, and thus to promptly execute an indwelling preparation operation for the indwelling needle for extracorporeal circulation 1. Moreover, as it is possible to move the inner needle 2 by operating the inner needle movement operation unit 31, it is possible to more readily move the inner needle 2 after puncture into a blood vessel.

When the inner needle movement operation unit 31 is sufficiently slid, the engaged member 31a is engaged with the housing engagement portion 34b, as indicated by the long dashed double-short dashed line in FIG. 4, whereby the inner needle 2 is held so as not to be displaced from the housed position. With the above, it is possible to achieve proper positioning of the inner needle 2 in the housed position. Thus, it is possible to promptly execute an operation for moving the inner needle 2 from the projecting position to the housed position after puncture into a blood vessel, and to efficiently execute an indwelling preparation operation for the indwelling needle for extracorporeal circulation 1. Further, it is possible to avoid unintentional displacement of the inner needle 2 once positioned. With the above, it is possible to avoid inconvenience that the puncture portion 2d projects from the outer needle tip end portion 14 while the outer needle 3 is indwelling in a blood vessel, and resultantly, that the projecting puncture portion 2d damages the inside wall of the blood vessel.

Figure 5:
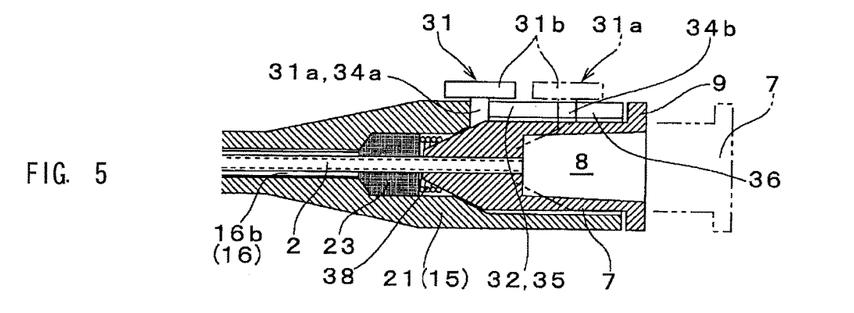
FIG. 5 is a diagram explaining major members of an indwelling needle for extracorporeal circulation having an urging member for urging a second connection portion.

In the second embodiment, there may be provided an urging member 38 for urging the inner needle connection portion 7 in a direction from the projecting position to the housed position. For example, in a modified example of the second embodiment shown in FIG. 5, an urging member 38 made of a coil spring is provided between the outer needle connection portion 15 and the inner needle connection portion 7, and a tapered connection portion between the inner needle 2 and the inner needle connection portion 7 is positioned inside the urging member 38. Then, one end portion of the urging member 38 is engaged with the seal member 23, and the other with the inner needle connection portion 7, whereby the inner needle connection portion 7 is urged by the urging force of the urging member 38 from the projecting position to the housed position. With this urging member 38 provided, when the inner needle movement operation unit 31 is slid with the inner needle 2 held in the projecting position to thereby release engagement between the engaged member 31a and the projecting engagement portion 34a, the inner needle connection portion 7 is urged by the urging force of the urging member 38, whereby the inner needle 2 moves from the projecting position to the housed position. Further, the engaged member 31a is caused to be engaged with the housing engagement portion 34b due to the moving force of the inner needle 2 whereby the inner needle 2 is held so as not to be displaced from the housed position. With the above, it is possible to move the inner needle 2 to the housed position with only a one-touch operation for releasing the engaged member 31a engaged with the projecting engagement portion 34a. Thus, it is possible to more promptly complete an indwelling preparation operation for the indwelling needle for extracorporeal circulation 1.

Note that the urging member in the present invention is not limited to an urging member made of a coil spring. That is, so long as it is possible to urge the inner needle connection portion 7 in a direction from the projecting position to the housed position, any urging member having any structure can be employed. For example, when a sleeve-like projection is formed as an urging member projecting from a rubber seal member 23 toward the inner needle connection portion 7 side, the projecting end portion of the sleeve projection is held abutting on the inner needle connection portion 7, and the inner needle 2 is moved to the projecting position, the sleeve projection is compressed along the movement direction of the inner needle 2. Then, when the engaged member 31a in the projecting position is released from the projecting engagement portion 34a, the inner needle connection portion 7 is urged to move to the housed position by a restoring force of the sleeve projection in a compressed state.

In the second embodiment and the modified example thereof, when a projection is formed on the front surface (a position touched by a finger or the like in operation) of the movement operation piece 31b of the inner needle movement operation unit 31, a finger can be readily hooked on the inner needle movement operation unit 31. This is preferable, as operability in moving the inner needle 2 can be improved. Further, although the inner needle connection portion 7 has the engaged member 31a and the outer needle connection portion 15 has the engagement portion 34, the present invention is not limited to this structure. That is, any structure in which one of the outer needle connection portion 15 and the inner needle connection portion 7 has an engaged member and the other has an engagement portion is applicable. That is, a structure, for example, in which the inner needle connection portion 7 has an engagement portion and the outer needle connection portion 15 has an engaged member is applicable.

Further, the structure of the engaged member 31a and the engagement portion 34 is not limited to the structure described in the second embodiment and the modified example. For example, a nail-like engaged member may be provided to one end portion of a swingable plate, an engagement operation unit adapted to a swing operation by an operator may be provided to the other end, and an engagement portion may be formed as a recess with which the nail-like engaged member can be engaged. In order to release engagement between the engaged member and the engagement portion, the engagement operation unit may be operated to swing the plate to thereby release engagement between the engaged member and the engagement portion. In the above, provision of the urging member between the inner needle connection portion and the outer needle connection portion is preferable, as it is possible to move the inner needle 2 to the housed position with a one-touch operation relative to the engagement operation unit.

In the second embodiment and the modified example thereof, although the movement guide portion 32 (the engagement guide portion 35) guides the inner needle connection portion 7 and the engaged member 31a along the movement direction of the inner needle 2, the present invention is not limited to the above description. That is, any structure in which a movement guide portion guides the inner needle connection portion 7 and an engagement guide portion guides the engaged member 31a is applicable, and the movement guide portion and the engagement guide portion may be separately provided. For example, the housing space 21d of the outer needle connection portion 15 may be formed slightly larger than the inner needle connection portion 7 so that the inner needle connection portion 7 can slide on the inner circumferential surface of the connection portion main body 21 of the outer needle connection portion 15 along the movement direction of the inner needle 2. That is, the inner circumferential surface of the connection portion main body 21 may function as the movement guide portion in the present invention.

Note here that although a part of the inner needle movement operation unit 31 is used as the engaged member 31a in the second embodiment and the modified example thereof, the present invention is not limited to this structure. For example, an engaged member may be provided to the inner needle connection portion 7 separately from the inner needle movement operation unit 31. Further, although an indwelling needle for extracorporeal circulation 1 having a structure for guiding the inner needle 2 in movement (the movement guide portion 32), a structure for holding the inner needle 2 in a certain position (the engaged member 31a and the engagement portion 34), and a structure for operating to move the inner needle 2 (the inner needle movement operation unit 31) is described as an example in the second embodiment and the modified example thereof, the present invention is not limited to the above description. The indwelling needle for extracorporeal circulation may have a structure having at least one of the movement guide portion, the engaged member and the engagement portion, and the inner needle movement operation unit.

Figure 6A:
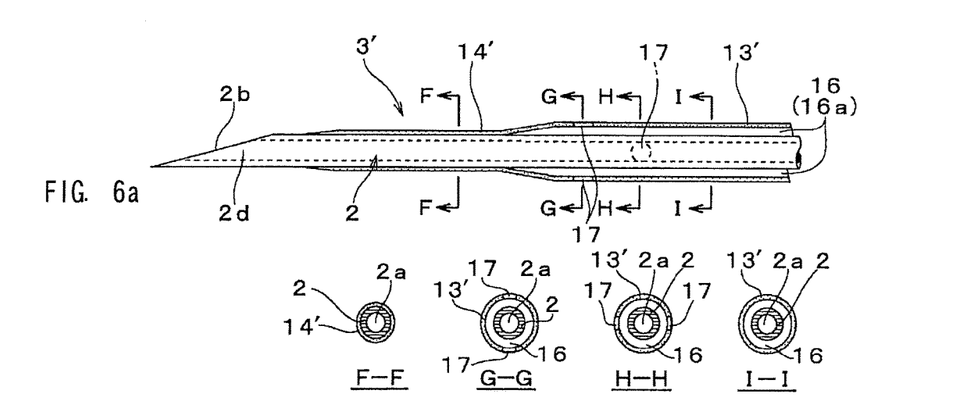
FIG. 6a is a diagram explaining an inner needle of an indwelling needle for extracorporeal circulation having moved to a projecting position and showing cross sections at respective positions, in which a holding member is formed by thinning the tip end portion of the outer needle main body so as to have a reduced diameter.
Figure 6B:
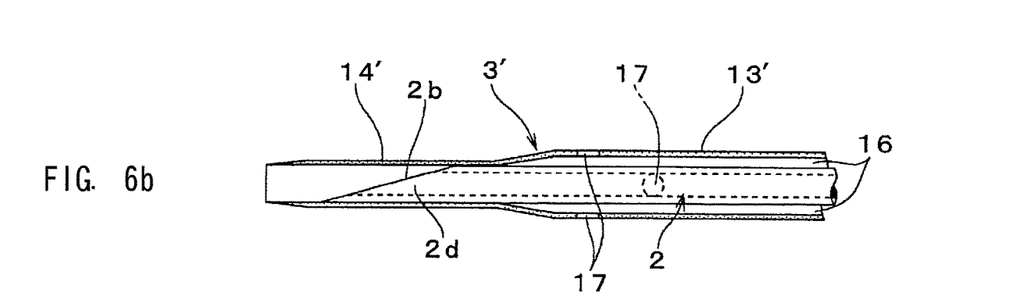
FIG. 6b is a diagram explaining an inner needle of an indwelling needle for extracorporeal circulation having moved to a housed position and showing cross sections at respective positions, in which a holding member is formed by thinning the tip end portion of the outer needle main body so as to have a reduced diameter.

Further, although the outer needle tip end portion 14 is attached to the tip end portion of the longitudinal tube-like outer needle main body 13 to form the outer needle 3 in the respective embodiments described above, the present invention is not limited to the above description. For example, in a third embodiment shown in FIG. 6, an outer needle tip end portion 14' may be formed by thinning the tip end portion of a tube-like outer needle main body 13' so as to have a smaller diameter in formation of an outer needle 3'. An outer needle 3' having the above-described reduced diameter structure does not require formation of the outer needle tip end portion 14' separately from the outer needle main body 13'. This can reduce manufacturing cost.

Although in the respective embodiments described above the outer diameter of the inner needle 2 is set smaller than the inner diameter of the outer needle 3, 3' to thereby form a cylindrical outer circumferential space 16 between the outer circumferential surface of the inner needle 2 and the inner circumferential surface of the outer needle 3, 3', the present invention is not limited to the above description. That is, any structure in which the outer circumferential space 16 where blood can flow in the present invention may be formed between the outer circumferential surface of the inner needle 2 and the inner circumferential surface of the outer needle 3, 3', and between the inner circumferential surface of the insertion space 21c and the outer circumferential surface of the inner needle 2 is applicable. For example, a groove may be formed on the outer circumferential surface of the inner needle 2 or a flat surface may be formed (formed such that the inner needle 2 has a D-shaped cross section) so that the space between the outer circumferential surface of the inner needle 2 and the inner circumferential surface of the outer needle 3, 3' and between the inner circumferential surface of the insertion space 21c and the outer circumferential surface of the inner needle 2 is defined as the outer circumferential space 16. However, when the space is too small, blood likely stops flowing, and thrombus may be caused. In view of the above, it is preferable that the outer circumferential space 16 is formed to be cylindrical so that blood is not likely to stop flowing, as shown in the respective embodiments.

Use of the indwelling needle for extracorporeal circulation according to the present invention is not limited to blood extracorporeal circulation in dialysis, mentioned as an example. That is, the present invention can be used in any situation for extracorporeal circulation of blood of a patient. For example, the present invention is applicable to apheresis treatment for separation to remove a specific component from blood, for example. Further, a projecting flat piece (a so-called "wing") may be formed projecting from a lateral side of an indwelling needle for extracorporeal circulation to facilitate securing of the indwelling needle for extracorporeal circulation on a patient, by means of tape.

It should be understood that the above-described embodiments are only examples in any sense, and not limiting. That is, the present invention is not limited to the above description, but is defined according to the claims attached, and includes any modifications equivalent thereto in meaning and scope.

REFERENCE SIGNS LIST 1 indwelling needle for extracorporeal circulation
2 inner needle
2a inner space
2b tip end opening
2c base end opening
2d puncture portion
3, 3' outer needle
4 blood circuit
4a lock ring
4b lock ring
7 inner needle connection portion
8 inner needle communicating space
9 inner needle side male thread
13, 13' outer needle main body
14, 14' outer needle tip end portion
14a penetrating space
14b joint portion
15 outer needle connection portion
16 outer circumferential space
16a tip end side part
16b base end side part
17 hole
21 connection portion main body
21a tip end portion
21b base end portion
21c insertion space
21d housing space
22 branched portion
22a branched communicating space
23 seal member
23a seal-penetrating hole
24 branch side male thread
31 inner needle movement operation unit
31a engaged member
31b movement operation piece
32 movement guide portion
34 engagement portion
34a projecting engagement portion
34b housed engagement portion
35 engagement guide portion
36 entry notch slit

The invention claimed is:

1. An indwelling needle for extracorporeal circulation having a double tube structure including an outer needle made of a tube member having an opening formed on a tip end thereof, and an inner needle made of a tube member having a puncture portion formed on a tip end thereof and inserted in the outer needle, comprising:
a holding member for closing in a liquid-tight state respective ends of an outer circumferential space formed between an outer circumferential surface of the inner needle and an inner circumferential surface of the outer needle, and for closely holding the inner needle in a slidable state;
a hole formed on an outer circumferential surface of the outer needle on a tip end side thereof in a position further rearward than the holding member, for communicating the inside of a blood vessel and the outer circumferential space when being punctured in the blood vessel;
a first connection portion for communicating the outer circumferential space and one end portion of a blood circuit; and
a second connection portion for communicating an inner space of the inner needle and another end portion of the blood circuit,
wherein
the inner needle is held by the holding member so as to move between a projecting position where a tip end portion thereof projects from a tip end of the outer needle and a housed position where the tip end portion thereof is housed in the outer needle,
the inner needle is punctured into the blood vessel while being held in the projecting position, and then moved to the housed position after being punctured so that blood extracorporeal circulation is able to be conducted via the first connection portion and the second connection portion,
the holding member includes a first holding member for closing in a liquid-tight state a tip end of the outer circumferential space, and a second holding member for closing in a liquid-tight state a base end of the outer circumferential space, and
the first holding member is fixed with respect to the outer needle, the inner needle is slidable with respect to the first holding member, and the first holding member is provided at a position nearer to the tip end than the hole.

2. The indwelling needle for extracorporeal circulation according to claim 1, wherein the hole is an inlet through which blood is to be introduced from the blood vessel, and
a tip end opening of the inner space of the inner needle is a return opening through which to return into the blood vessel blood having circulated in the blood circuit.

3. The indwelling needle for extracorporeal circulation according to claim 1, wherein the first connection portion has a movement guide portion for guiding the second connection portion along a movement direction of the inner needle.

4. The indwelling needle for extracorporeal circulation according to claim 1, wherein the second connection portion has an inner needle movement operation unit projecting toward an outside of the second connection portion.

5. The indwelling needle for extracorporeal circulation according to claim 1, further comprising an engagement guide portion provided between a projecting engagement portion and a housed engagement portion, for guiding an engaged member along a movement direction of the inner needle.

6. The indwelling needle for extracorporeal circulation according to claim 5, wherein
each of the projecting engagement portion and the housing engagement portion is defined by a hole having a diameter that is that is greater than a width size of the engagement guide portion, and
an entry notch slit formed on an extension line of the engagement guide portion has a width that is smaller than the width size of the engagement guide portion and smaller than a diameter of the engaged member.

7. The indwelling needle for extracorporeal circulation according to claim 1, further comprising
an urging member provided between the first connection portion and the second connection portion, for urging the inner needle in a direction from the projecting position to the housed position, wherein
when engagement between an engaged member and a projecting engagement portion is released, the second connection portion is urged by an urging force of the urging member whereby the inner needle moves from the projecting position to the housed position.

8. The indwelling needle for extracorporeal circulation according to claim 1, wherein an outer diameter of the inner needle is set smaller than an inner diameter of a longitudinal tube-like outer needle main body so that the outer circumferential space is formed to be cylindrical between the outer circumferential surface of the inner needle and an inner circumferential surface of the outer needle main body.

9. The indwelling needle for extracorporeal circulation according to claim 1, wherein
   one of the first connection portion and the second connection portion has an engaged member, and the other has an engagement portion with which the engaged member is able to be engaged, and
   the engagement portion includes a projecting engagement portion with which the engagement member is engaged when the inner needle is in the projecting position and a displacement of the inner needle from the projecting position is prevented, and a housed engagement portion with which the engaged member is engaged when the inner needle is in the housed position and a displacement of the inner needle from the housed position is prevented.

10. The indwelling needle for extracorporeal circulation according to claim 1, wherein
    the outer needle comprises an outer needle main body and an outer needle tip end portion formed from a material which is harder than that of the outer needle main body, and which is a member separate from the outer needle main body,
    the outer needle main body has an inner diameter which is a constant and which is larger than an outer diameter of the inner needle, and the hole is formed on an outer circumferential surface of the outer needle main body near the tip end portion, and
    the outer needle tip end portion has a constant inner diameter which is equal to or slightly smaller than the outer diameter of the inner needle, the outer needle tip end portion functions as the first holding member, and the tip end thereof has a tapered thin shape.

11. The indwelling needle for extracorporeal circulation according to claim 1, wherein
    an outer periphery of the tip end of the inner needle is covered by the first holding member in the housed position.

* * * * *